(12) United States Patent
Ballan

(10) Patent No.: US 6,981,872 B2
(45) Date of Patent: Jan. 3, 2006

(54) BONE IMPLANT METHOD OF IMPLANTING, AND KIT FOR USE IN MAKING IMPLANTS, PARTICULARLY USEFUL WITH RESPECT TO DENTAL IMPLANTS

(76) Inventor: Nabil Ballan, Kfar Eilabun, 16972 Lower Galillee (IL)

( * ) Notice: Subject to any disclaimer, the term of this patent is extended or adjusted under 35 U.S.C. 154(b) by 263 days.

(21) Appl. No.: 10/332,841

(22) PCT Filed: Jul. 11, 2001

(86) PCT No.: PCT/IL01/00637

§ 371 (c)(1),
(2), (4) Date: Jan. 14, 2003

(87) PCT Pub. No.: WO02/07633

PCT Pub. Date: Jan. 31, 2002

(65) Prior Publication Data

US 2005/0026112 A1 Feb. 3, 2005

(30) Foreign Application Priority Data

Jul. 19, 2000 (IL) ..................................... 137380

(51) Int. Cl.
*A61C 8/00* (2006.01)

(52) U.S. Cl. ..................................................... 433/173
(58) Field of Classification Search ................ 433/172, 433/173, 174, 175, 176

See application file for complete search history.

(56) References Cited

U.S. PATENT DOCUMENTS

| | | |
|---|---|---|
| 5,100,323 A | 3/1992 | Friedman et al. |
| 5,221,204 A | 6/1993 | Kruger et al. |
| 5,873,721 A | 2/1999 | Willoughby |
| 5,975,903 A | 11/1999 | Shoher et al. |
| 6,287,118 B1 | 9/2001 | Naganuma et al. |

*Primary Examiner*—Cary E. O'Connor

(57) ABSTRACT

A dental bone implant includes: a main implant segment to be received in a cavity which may be of relatively shallow depth, formed in the jawbone, and a lateral implant segment having one end to be seated on the main implant segment, and an opposite end formed with projections to be received in grooves formed in the jawbone laterally of the cavity for providing lateral support of the main implant segment when implanted into the bone. Also described is a method of making dental implants and a kit useful therefor.

17 Claims, 13 Drawing Sheets

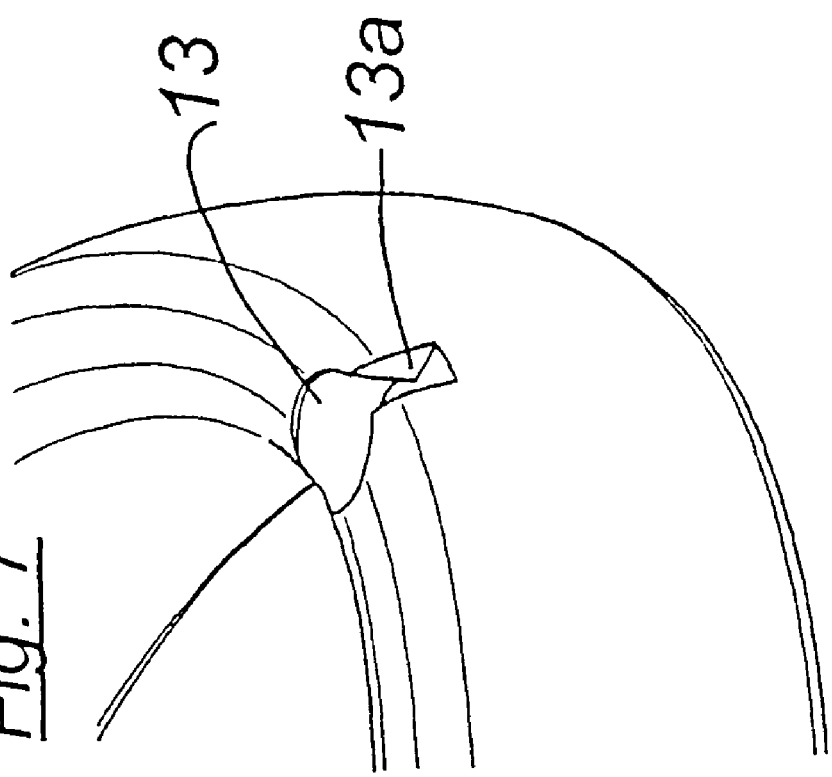
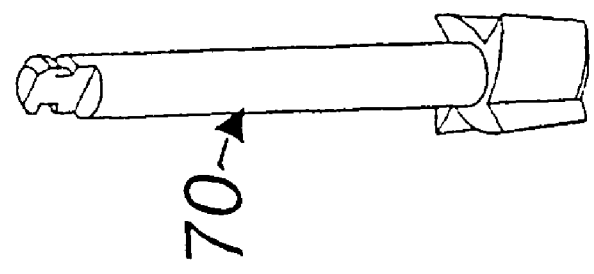
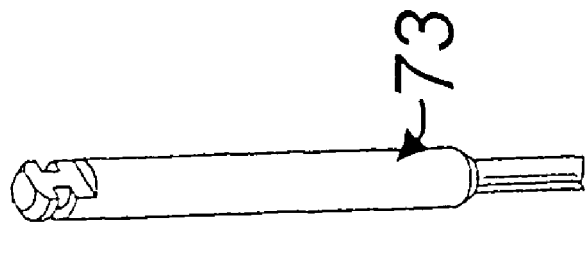

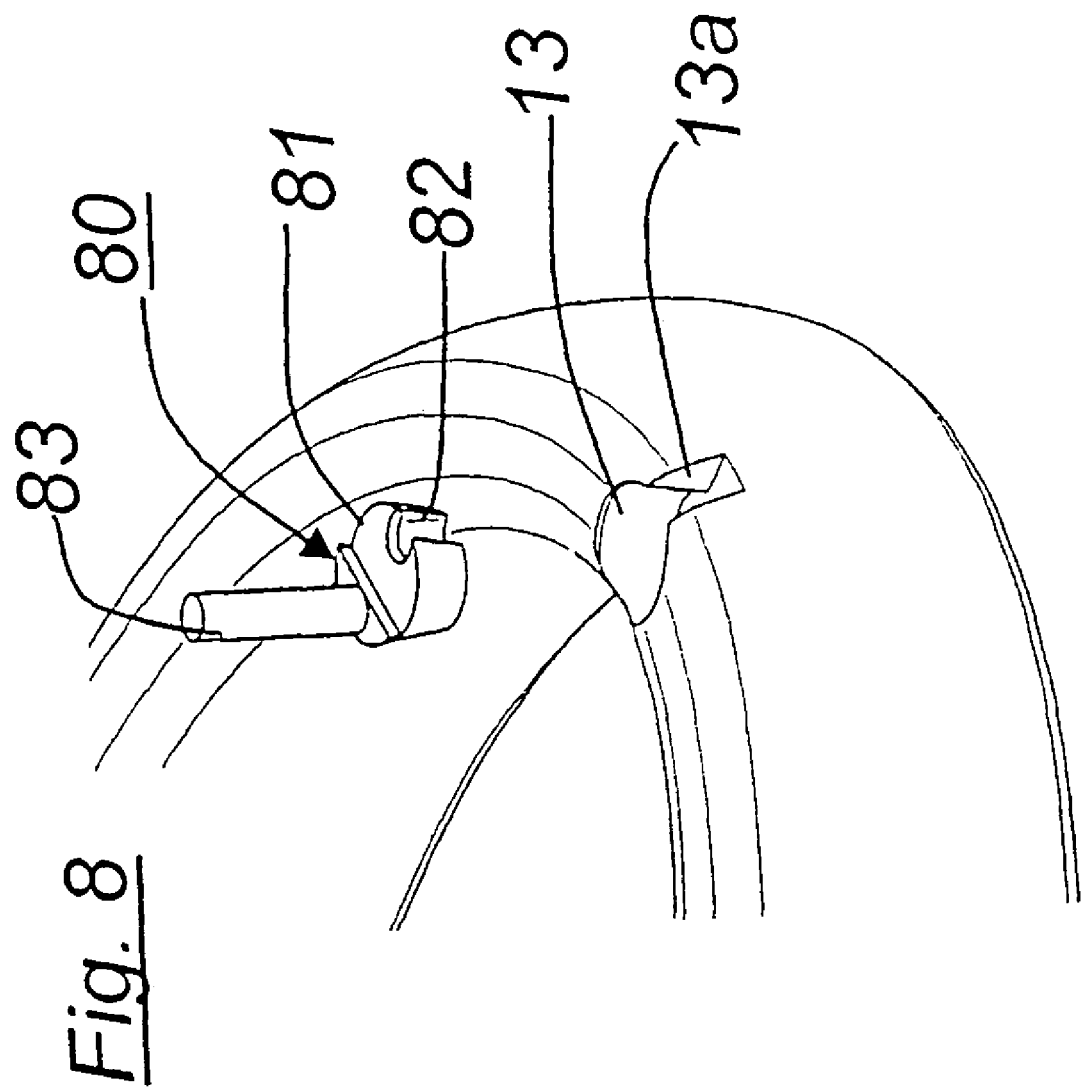

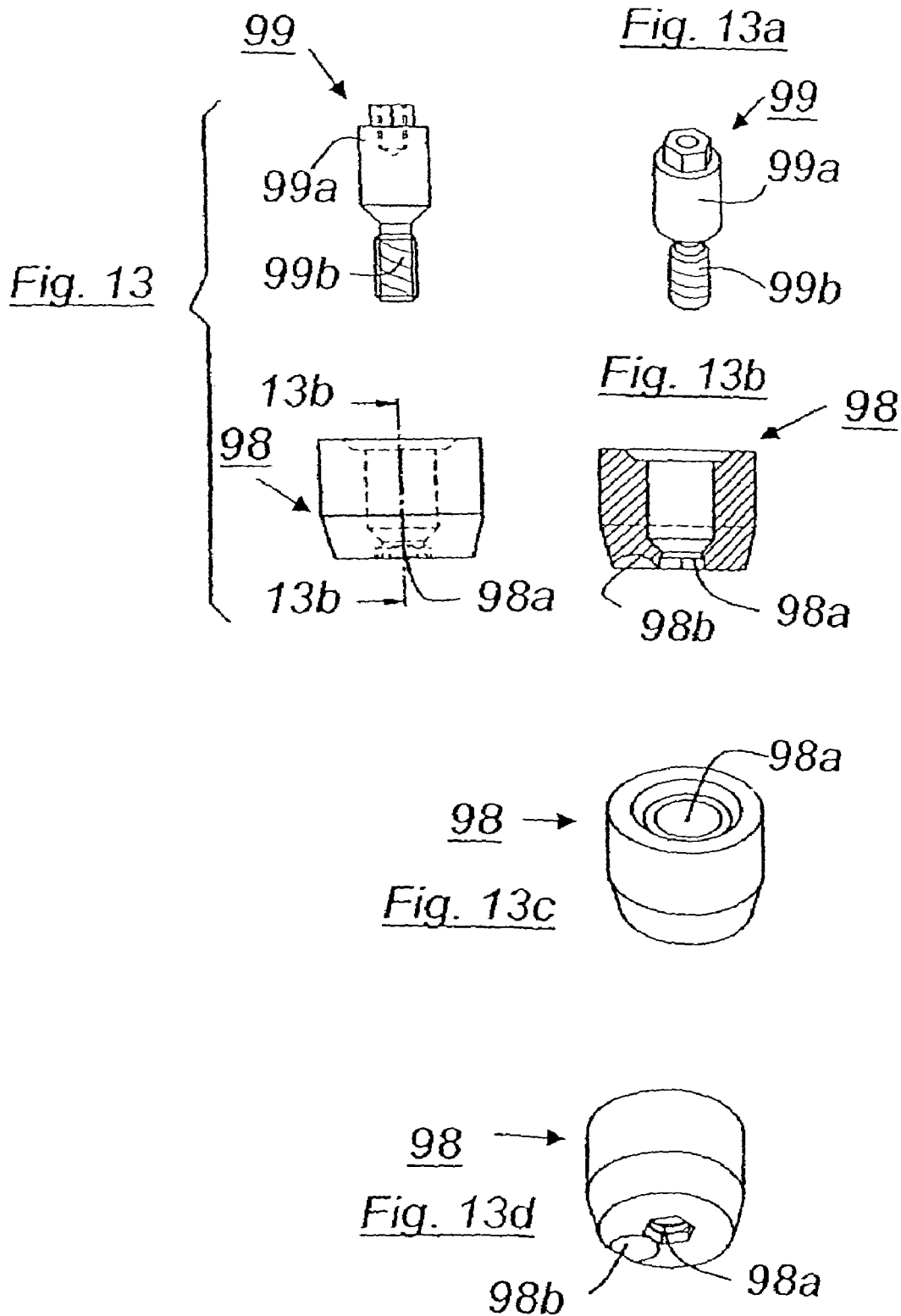

BONE IMPLANT METHOD OF IMPLANTING, AND KIT FOR USE IN MAKING IMPLANTS, PARTICULARLY USEFUL WITH RESPECT TO DENTAL IMPLANTS

FIELD AND BACKGROUND OF THE INVENTION

The present invention relates to bone implants, and also to a method of implantation, and to a kit for use in creating implant sites in bones. The invention is particularly useful in dental implants and is therefore described below with respect to this application.

Dental implants are increasingly being used where a patient requires a prosthetic device to bold one or more artificial teeth in place. Conventional implants include a cylindrical pin, usually of titanium but of other compatible material, formed with a threaded (or other shaped) bore implanted into the jawbone and covered by a temporary cap for a sufficient period of time to permit osseointegration of the implant with the bone, usually about three months for the mandible (lower jaw) and about six months for the maxilla (upper jaw). After this period of time, the cap is removed and the threaded bore is used to receive a post serving as an abutment which provides a support site for one or more artificial teeth.

The conventional dental implants, however, suffer from a number of drawbacks. Thus the strength and stabilization of the implant is greatly dependent on the anchoring method in the jawbone. For this reason, the bore drilled in the jawbone for receiving implant is as long as possible, generally extending through both the outer compact bone tissue and the inner medullary or soft spongy tissue of the jawbone. However, the latter tissue does not provide strong support for the implant, and therefore the implant may have insufficient strength and stabilization particularly with respect to patients having relatively shallow jawbones.

In addition, drilling long bores increases the danger of overheating during drilling, which could result in serious bone damage. Also, drilling long bores generally requires frequent raising and lowering the drill for cooling purposes, which can create misregistration in the resulting sections of the bore. There is also a danger of non-parallelism with respect to a plurality of implants and abutments, which could result in an unequal distribution of the stresses, overloading, and failure.

OBJECTS AND BRIEF SUMMARY OF THE PRESENT INVENTION

An object of the present invention is to provide a bone implant generally, and a dental implant in particular, having advantages in one or more of the above respects. Other objects of the invention are to provide a method of implantation, and also a kit particularly useful with respect to the novel dental implant.

According to one aspect of the present invention, there is provided a bone implant comprising: a main implant segment to be received in a cavity formed in a first face of the bone, and a lateral implant segment having one end to be seated on the main implant segment, and carrying at its opposite end at least one projection to be received in a groove formed in a second face of the bone laterally of the cavity for providing lateral support of the main implant segment when implanted into the bone.

According to further features in the preferred embodiment of the invention described below, the main implant segment is formed with a central bore in one end face for attaching a prosthetic device thereto when the main implant segment is implanted into the bone, and with a lateral slot extending along one side of the main implant segment from the one end face to the opposite end face of the main implant segment for receiving the lateral implant segment.

According to further preferred features, the main implant segment is of conical configuration. In addition, there are a plurality of projections at the end of the lateral implant segment, the projections being in the form of spaced parallel ribs receivable in a plurality of correspondingly-formed grooves in the bone.

The two part (segment) construction of the present invention provides a number of important advantages over the conventional one-part construction. A particularly important advantage is that the lateral implant segment combined with the conical implant segment have a greater contact area and a smaller displacement (volume), thus minimizing impact on bone structure and maximizing bonding and osseointegration.

Such a construction is particularly useful in dental implants since it enables the dental implant to be made of a substantially shorter vertical height, as compared to the conventional dental implants, and still provide sufficient strength and stabilization needed for implants. For example, in such an implant, the main implant segment may be of a short height so as to be contained substantially only within the outer compact bone tissue of the jawbone, and not to penetrate into the inner medullar or soft spongy tissue of the jawbone, as lateral support is provided by the lateral implant segment.

According to another aspect of the present invention, there is provided a method of making an implant in a bone of a subject, comprising: drilling a cavity in a first face of the bone; forming at least one groove in a second face of the bone laterally of the cavity; inserting into the cavity a main implant segment formed with a lateral slot extending through and along one side of the main implant segment from one end face to the opposite end face thereof; seating on said one end face of the main implant segment one end of a lateral implant segment with the lateral segment extending along the lateral slot past the opposite end face of the main implant segment and formed with at least one projection to be received in the groove formed in the bone; and securing the lateral implant segment to the main implant segment for a period of time to permit osseointegration of the segments to the bone. A prosthetic device may then be attached to the main implant segment.

The method is particularly useful in dental implants whereupon the socket is formed in the jawbone to a relatively shallow depth such as to terminate short of the inner medullary or soft spongy tissue of the jawbone. Since such a dental implant and method of implantation do not require that deep bores be drilled in a jawbone, the implant and method decrease the danger of overheating during drilling, imprecision in the drilled bore, non-parallelism when a plurality of implants are provided, and thereby the danger of unequal stress distribution.

According to a still further aspect of the present invention, there is provided a kit for use in making implants, comprising: a main implant segment to be received in a cavity in the bone; and a lateral implant segment to be seated at one end on the main implant segment, and carrying at least one projection at the opposite end to be received in a groove formed in the bone laterally of the cavity for providing lateral support to the main implant segment when implanted into the bone.

According to further features in the described preferred embodiment, the kit may further include: a cover to be applied over both segments; a fixation screw for securing the cover to both segments; an accessory to be received in the cavity in the bone and having the same configuration as the main implant segment; and a supporting fixture mountable on the accessory for supporting a grooving device laterally of the cavity to produce at least one groove in the bone for receiving the projection of the lateral implant segment.

Further features and advantages of the invention will be apparent from the description below.

BRIEF DESCRIPTION OF THE DRAWINGS

The invention is herein described, by way of example only, with reference to the accompanying drawings, wherein:

FIGS. 6 and 7 illustrate two stages in preparing and applying the implant;

FIGS. 7a and 7b illustrate two types of drills that may be used in the stage of FIG. 7;

FIGS. 8 and 9 illustrate two further stages in applying the implant;

FIG. 10a is a side view of a supporting fixture for supporting a grooving device used in the stage of FIG. 9, while

FIG. 13 is a side elevational, exploded view illustrating an abutment and pin applied to the implant after osseointegration of the implant segments with respect to the bone, FIG. 13a being a perspective view of the abutment pin, FIG. 13b being a sectional view of the abutment, and FIGS. 13c and 13d being perspective views of the abutment.

DESCRIPTION OF A PREFERRED EMBODIMENT

Figure 1:
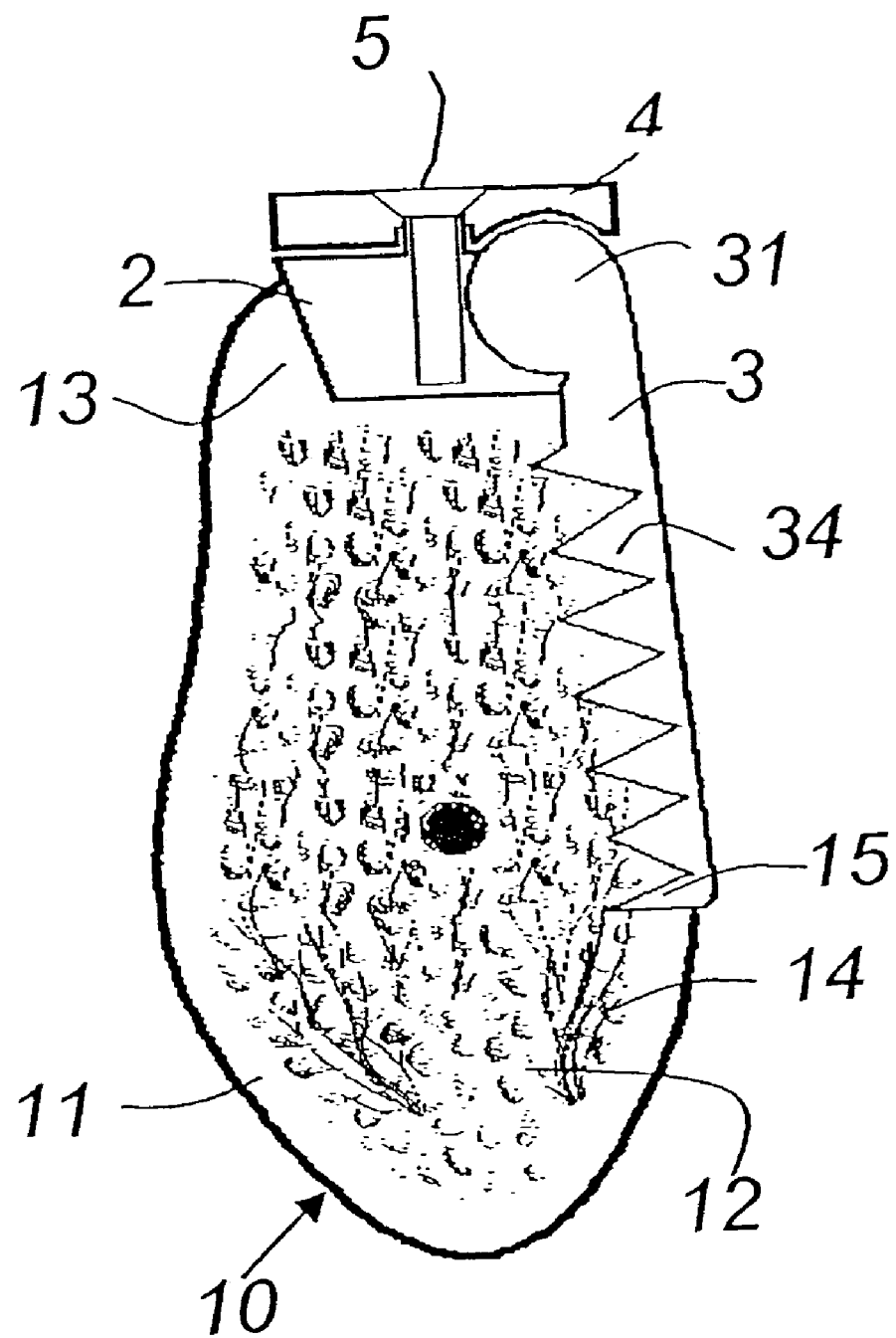
FIG. 1 is a sectional view illustrating one form of dental implant constructed in accordance with the present invention.

FIG. 1 illustrates one form of dental implant constructed in accordance with the present invention after it has been implanted in the jawbone and is to be used, after the osseointegration period (e.g., three months for the mandible and six months for the maxilla), for attaching a prosthesis device, such as an abutment for one or more artificial teeth.

As shown in FIG. 1, the illustrated dental implant includes the following parts: a main implant segment, generally designated 2, for implanting in a cavity drilled in the jawbone; a lateral implant segment, generally designated 3, for providing lateral support for the main implant segment when implanted in the jawbone; a cover, generally designated 4, for covering and securing the two segments during the period of osseointegration; and a fixation pin 5 for fixing the cover to the two segments during the osseointegration period.

In FIG. 1, the jawbone receiving the implant is generally designated 10. It consists of outer compact bone tissue 11 and inner medullar or soft spongy tissue 12. As shown in FIG. 1, the main implant segment 2 is received within a socket 13 formed in one face of the outer compact bone tissue 11. The lateral implant segment 3 has one end seated within the main implant segment 2, whereas the opposite end extends along another face 14 of the compact bone tissue and terminates in a plurality of ribs received within a plurality of grooves 15 formed in that face of the jawbone. As will be described more particularly below, such a dental implant construction enables the implant to be of short height so as to be contained substantially only within the outer compact bone tissue of the jawbone, while the lateral implant segment 3 provides lateral support for the main implant segment 2.

Figure 2:
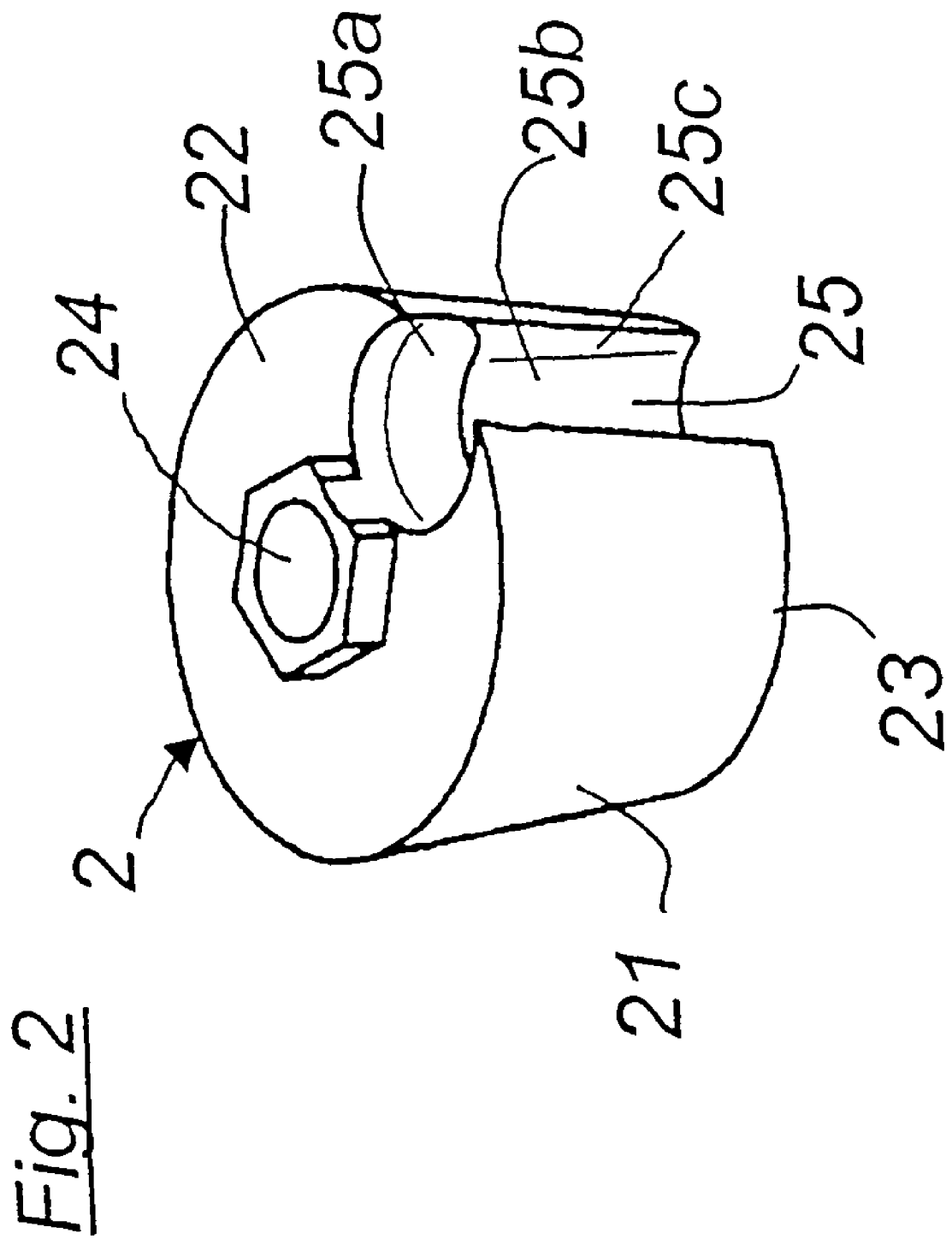
FIG. 2 more particularly illustrates the construction of the main implant segment in the implant of FIG. 1.

As shown particularly in FIG. 2, the main implant segment 2 is of conical configuration. It is formed with a conical surface 21, and with flat end faces at its opposite ends 22, 23. Conical segment 2 is further formed with a central tapped bore 24 extending through its end face 22 but terminating short of its end face 23, and with a lateral slot or recess 25 extending along one side of the conical segment from one end face 22 through its opposite end face 23.

Lateral slot 25 includes two sections: a rounded or substantially semi-spherical section 25a adjacent to its end face 22, and a generally cylindrical or semi-cylindrical section 25b extending along the side of the segment to its opposite end face 23.

Semi-cylindrical slot section 25b is preferably formed with two opposed parallel flat faces, one of which is shown at 25c, to prevent turning of the lateral segment about its own axis within the conical segment 2.

Figure 3:
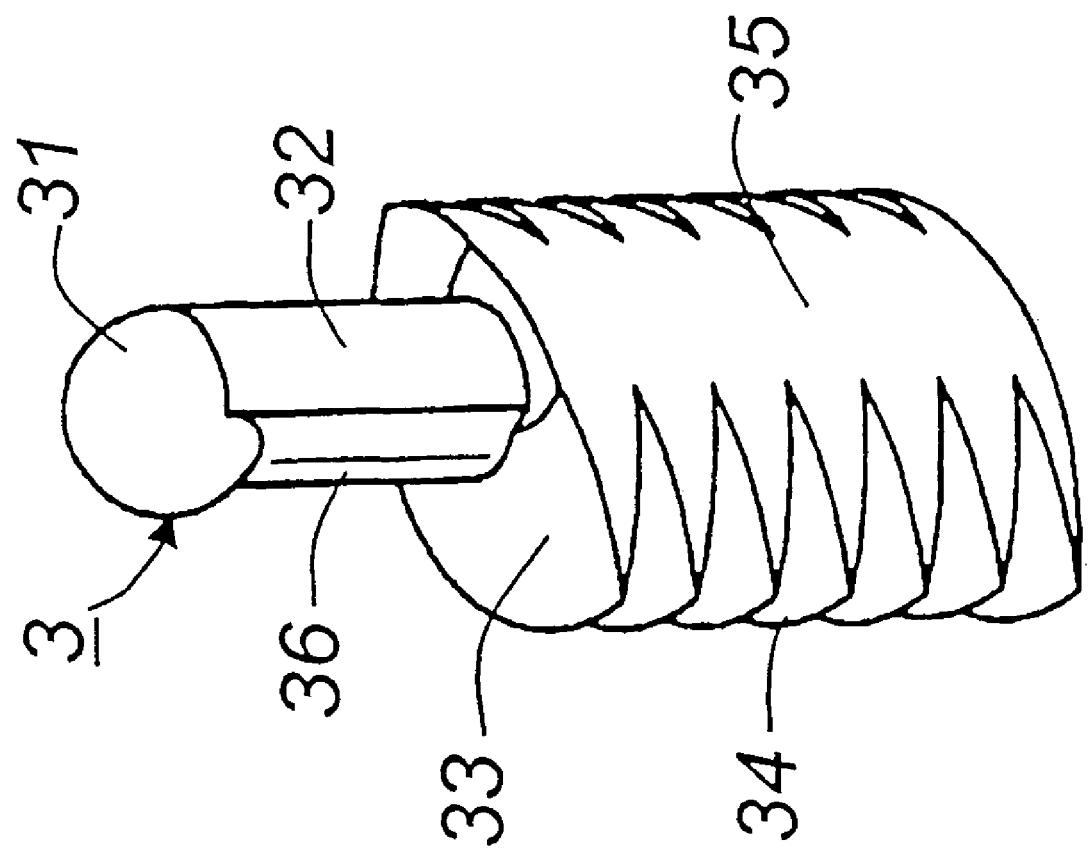
FIG. 3 more particularly illustrates the construction of the lateral implant segment in the implant of FIG. 1.

FIG. 3 more particularly illustrates the lateral segment 3, wherein it will be seen that it includes a rounded or substantially spherical section 31 at one end joined by a neck 32 to a ribbed section 33 at its opposite end. The ribbed section 33 is formed on its inner face with a plurality (seven being shown) tapered ribs 34 extending transversely and spaced longitudinally of that section for reception in the parallel grooves 15 (FIG. 1) formed in the jawbone 10. The outer face 35 of the ribbed section 33 is smooth and rounded to substantially conform to the contour of the inner face 14 of the jawbone.

As will be described more particularly below, the lateral segment 3 is applied to the conical segment 2 with the rounded end section 31 of the lateral segment seated in the rounded section 25a of the lateral recess 25 in the conical segment, with neck 32 of the lateral segment received within the semi-cylindrical slot section 25b of the conical segment, and with the ribbed section 33 of the lateral segment extending past the end 23 of the conical section to be received in the grooves 15 formed in the jawbone. Neck 32 is preferably formed with opposed, parallel, flat faces (one of which is shown at 36) engageable with flat faces 25c at the recess section to prevent turning. The arrangement is such that the lateral segment 3 provides substantial additional support for the conical segment 2 in the implant, thereby enabling the conical segment be of a relatively short height.

Figure 4A:
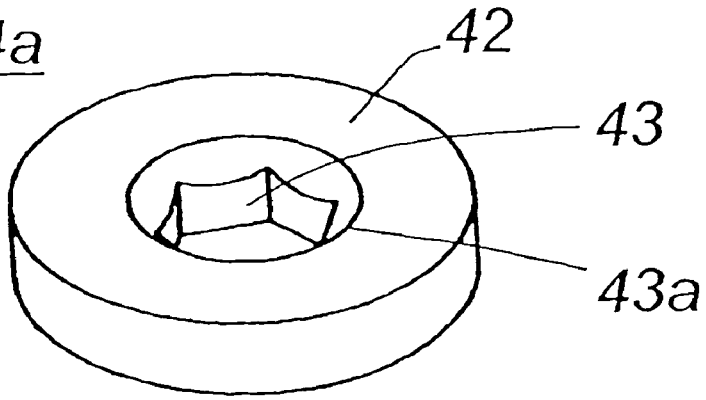
FIGS. 4a and 4b more particularly illustrate the opposite faces of the cover in the dental implant of FIG. 1.
Figure 4B:
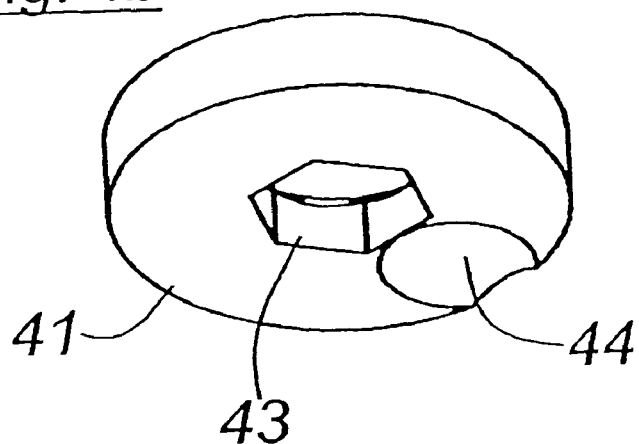

FIG. 4a illustrates the outer face 42 of the cover 4, while FIG. 4b illustrates the inner face 41 facing the conical segment 2 and the lateral segment 3. It will be seen that the cover is formed with a central, hexagonal bore 43 to be aligned with bore 24 of the conical segment 2. In addition, the inner face 41 is provided with a rounded or semi-spherical recess 44 to accommodate the round end 31 of the lateral segment 3 when applied to the conical segment 2. Bore 43 is beveled in the outer face 42 of the cover, as shown at 43a in FIG. 4a, to accommodate the beveled head of the fixation screw 5.

Figure 5:
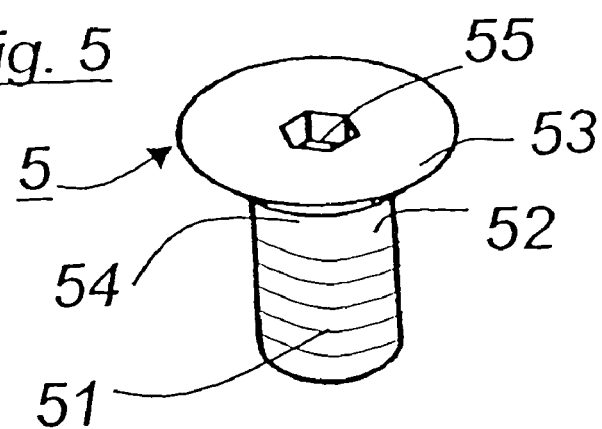
FIG. 5 illustrates the fixation screw for securing the cover to the implant segments in the implant of FIG. 1.

The fixation screw 5 is more particularly illustrated in FIG. 5. It includes a threaded shank 51 to be received through bore 43 in cover 4 and bore 24 in the conical segment 2. The threaded shank 51 is joined by neck 52 to an enlarged head 53 having an inner beveled surface 54 complimentary to the beveled surface 43a of cover of 4. Head 53 is formed with a hexagonal slot 55 on its outer surface for turning the screw.

IMPLANTATION PROCEDURE

Figure 14:
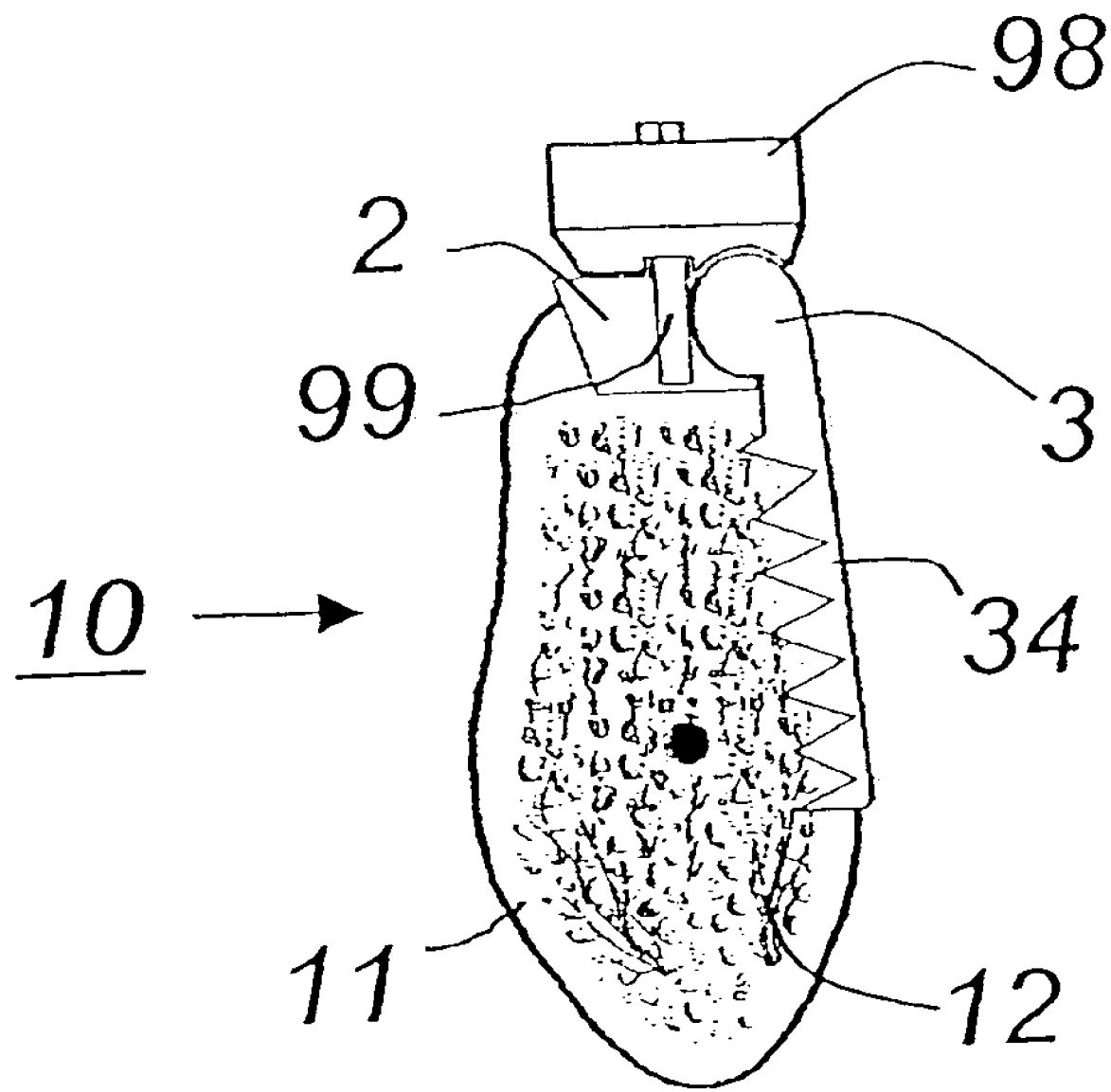
FIG. 14 is a sectional view illustrating the bone with the implant segments and abutment applied thereto preparatory to the application of a prosthetic device to the implant.

FIGS. 6–12 illustrate various stages in applying the dental implant described above with respect to FIGS. 1–5 into the jawbone 10 of a patient, as well as various accessories for facilitating the application of the dental implant. FIGS. 13 and 13a–13d illustrate an abutment that may be applied to the implant after the period of osseointegration, and FIG. 14 illustrates the jawbone 10 with the foregoing implant components applied preparatory to receiving the prosthesis.

Figure 6:
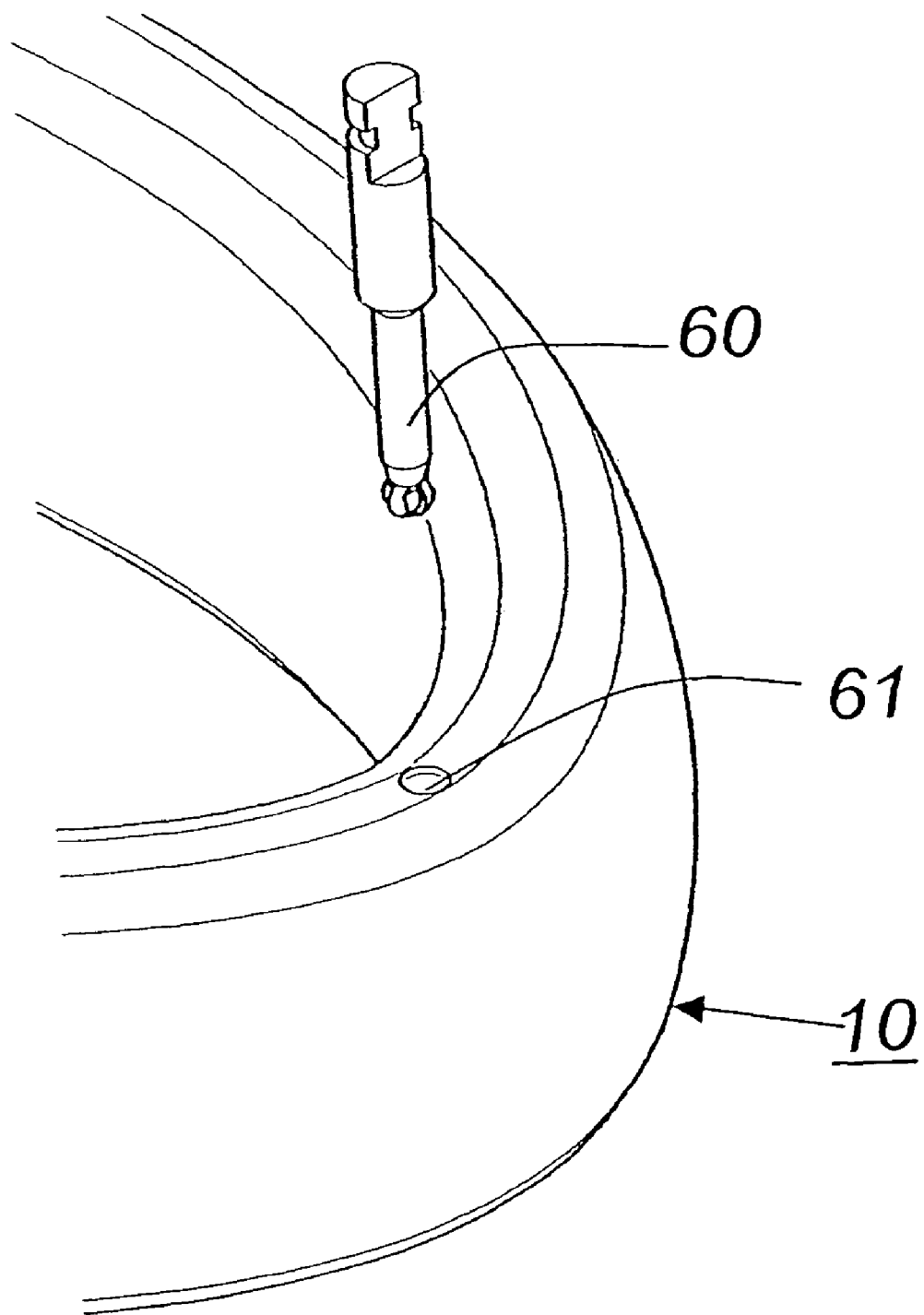

As shown in FIG. 6, the first step is to apply a guide drill 60 to the jawbone to mark the bone with an impression 61 where the implant is to be placed.

A conical drill 70 (FIG. 7a) is then applied to produce a cavity 13 having the conical shape of the conical segment 2 (FIGS. 1 and 2). The cavity 13 produced by conical drill 70 penetrates only for a short depth into the jawbone, namely through the compact bone tissue 11, and does not penetrate through the medullary or soft spongy bone tissue 12.

After the conical cavity 13 is formed in the bone, a cylindrical drill 73 (FIG. 7b) is used to produce a groove 13a (FIG. 7) through the inner side of the jawbone contiguous to the conical cavity 13. An accessory 80 (FIG. 8) is then inserted into the conical cavity 13 for use as a guide for forming the parallel spaced grooves 15 (FIG. 1) in the bone for receiving the ribs 34 of the lateral implant segment 3. As shown in FIG. 8, the accessory 80 is of the same conical shape as the conical implant segment 2 (FIG. 2), including a lateral slot 82, except that accessory 80 is not formed with a central bore as in the conical implant segment (shown at 24, FIG. 2), but rather with a finger piece 83 to facilitate handling the accessory. The accessory 80 is inserted into the conical socket 13 and is oriented such that its lateral slot 82, of the same shape as lateral slot 25 in the conical implant segment 2 (FIG. 2) is aligned with the portion of the jawbone to receive the lateral implant segment 3.

For normal sized jawbones, the bore 24 in the conical implant segment 2 would be formed centrally of that segment. For narrow jawbones, the conical implant segment 2 would preferably be of smaller diameter, and the bore 24 would be formed therethrough slightly off-center with respect to the implant segment but located substantially centrally of the jawbone 10. Preferably, the kit would include the various implant segments in different widths and lengths to accommodate a wide range of jawbone sizes.

Figure 9:
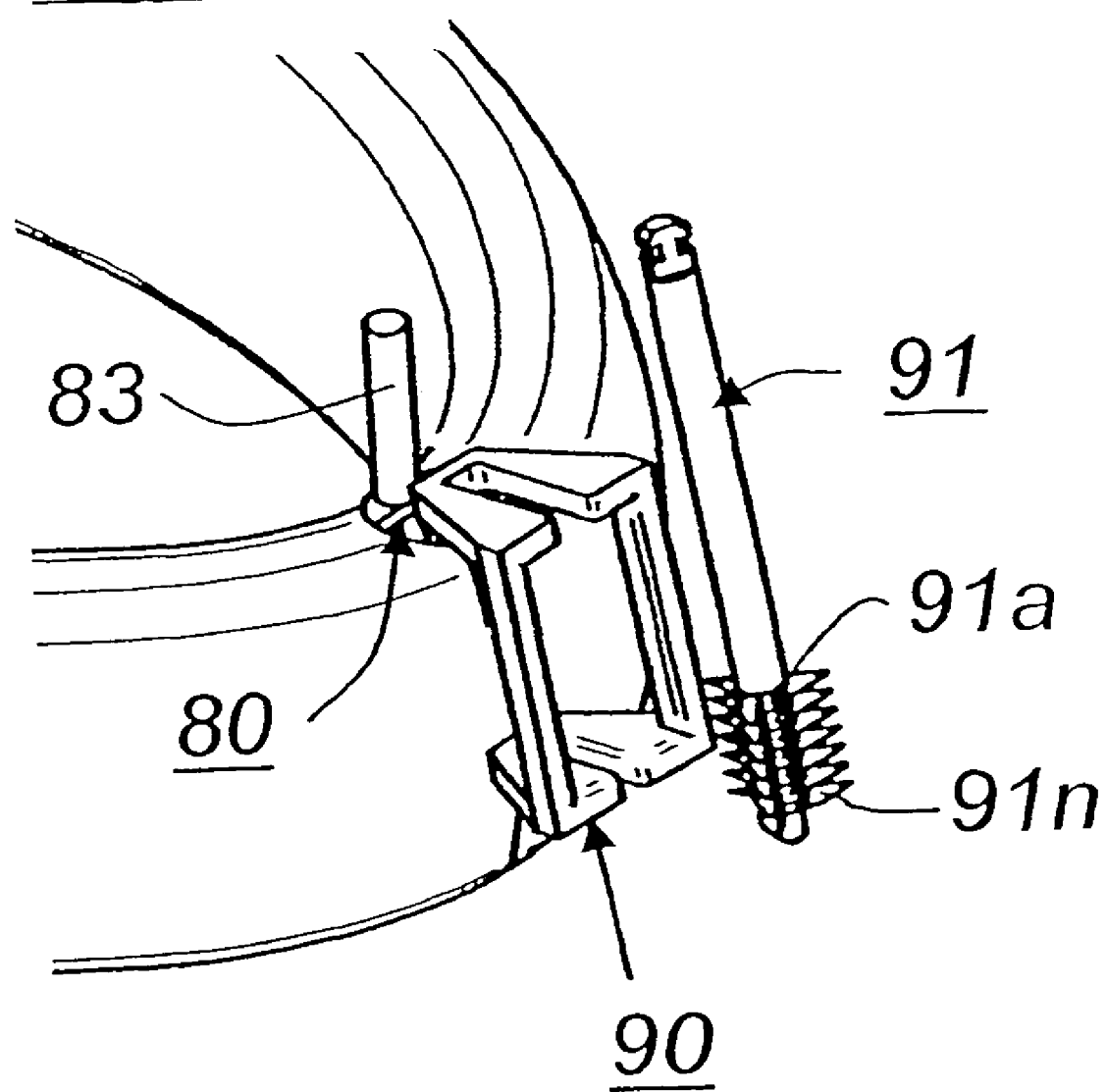

A supporting fixture, generally designated 90 in FIG. 9, is then inserted into the lateral slot 82 of the conical head 81, and is used as a guide for a grooving device 91 for forming the plurality (seven in this example) of grooves 15 for the ribs 34 of the lateral implant segment 3. The construction of the guide fixtures 90 is more particularly illustrated in FIGS. 10a–10b.

Figure 10A:
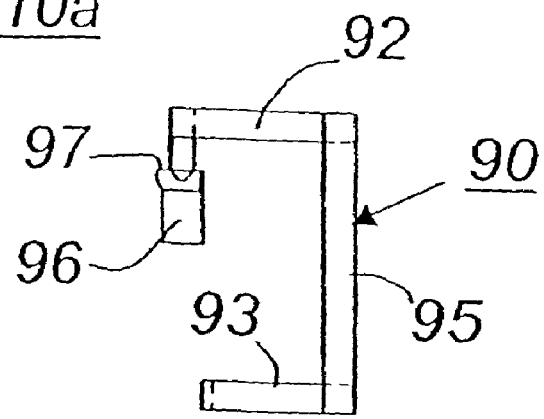
Figure 10B:
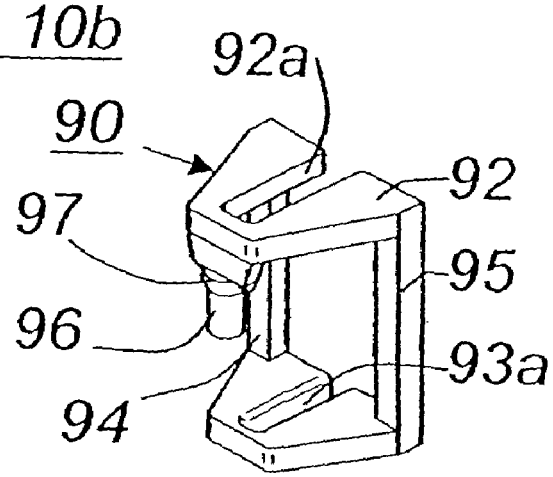
FIGS. 10b and 10c are perspective views more particularly illustrating the supporting fixture.
Figure 10C:
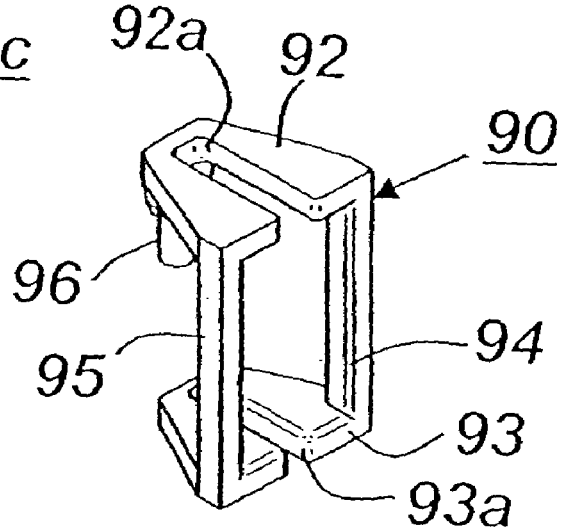

Thus, as shown in FIGS. 10a–10c, the supporting fixture 90 includes a pair of plates 92, 93 supported in spaced parallel relationship by a pair of parallel posts 94, 95. Each of the plates 92, 93 is formed with an open slot 92a, 93a, which slots are aligned with each other. Plate 92 is further formed with a depending pin 96 at the closed end of its respective slot 92a joined to the plate by a rounded juncture 97.

The supporting fixture 90 is mounted on the accessory 80 by inserting the depending pin 96 of the fixture into the lateral slot 82 of the accessory, with the rounded juncture 97 of the fixture seated on the upper surface 81 of the accessory. When the fixture 90 is so mounted, the two open slots 92a, 93a are aligned with the lateral slot 13a in the jawbone to thereby align the grooving device 91 with the surface of the jawbone in which the seven parallel grooves 15 are to be formed for receiving the ribs 34 of the lateral implant segment 3.

Grooving device 91 is formed at its lower end with a plurality of grooving elements 91a–91n, one for each of the grooves 15 to be formed in the jawbone 10 (FIG. 1). In this example, there are seven of such grooving elements, but it will be appreciated that this number could be larger or smaller, according to the size of the jawbone of the subject. It is contemplated that the kit would include various sizes of the grooving devices including various numbers of grooving elements to enable the appropriate device to be selected for the respective subject.

Thus, when the grooves 15 are to be formed in the subject's jawbone 10, the shank of the grooving device 91 is received within the aligned slots 92a, 93a of the supporting fixture 90, to align the grooving elements 91a–91n with the portion of the jawbone in which the grooves 15 are to be formed. The grooving device 91 may then be pressed against the jawbone, being guided by the slots 92a, 93a, to cause the grooving elements 91a–91n to form the grooves 15 in the jawbone. Such a grooving device is capable of producing grooves in the jawbone precisely matching the plurality of ribs 34 on the lateral implant segment 3 with a minimum of overheating.

Figure 11:
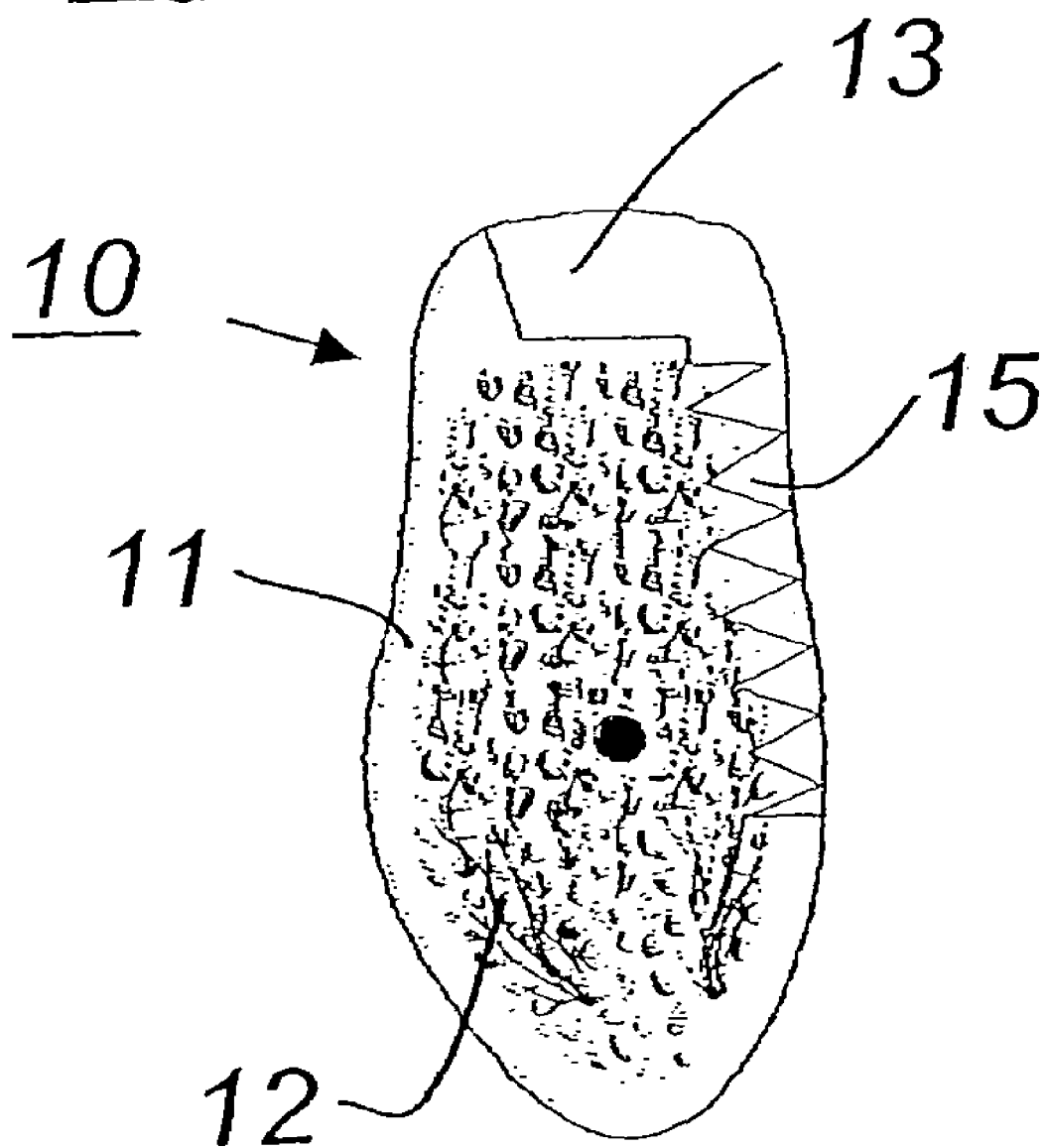
FIG. 11 illustrates the dental jawbone section after being formed with the cavity and with the groove for receiving the main implant segment and the lateral implant segment.
Figure 12:
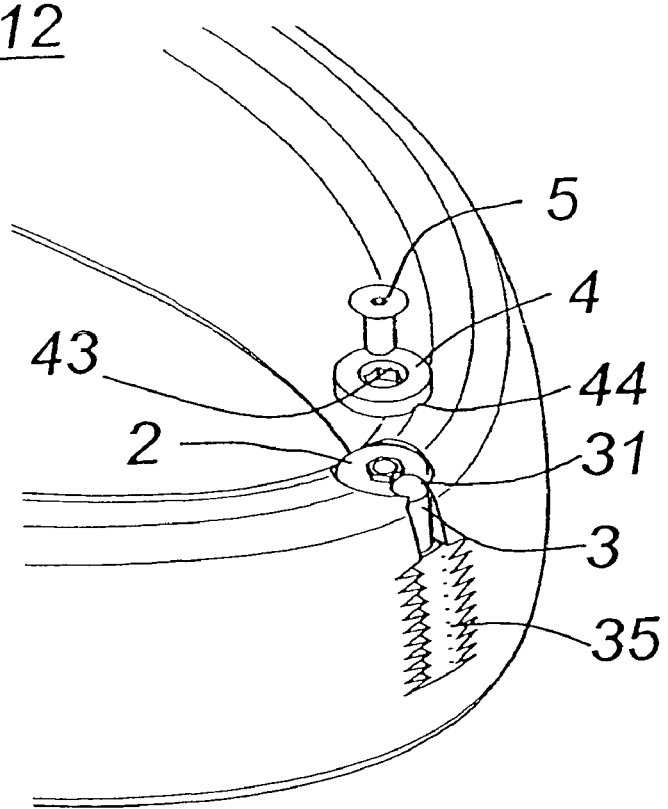
FIG. 12 is an exploded view illustrating the manner of assembling the implant segments within the cavity formed in the bone, FIG. 12a illustrating the implant segments after having been received in the cavity.
Figure 12A:
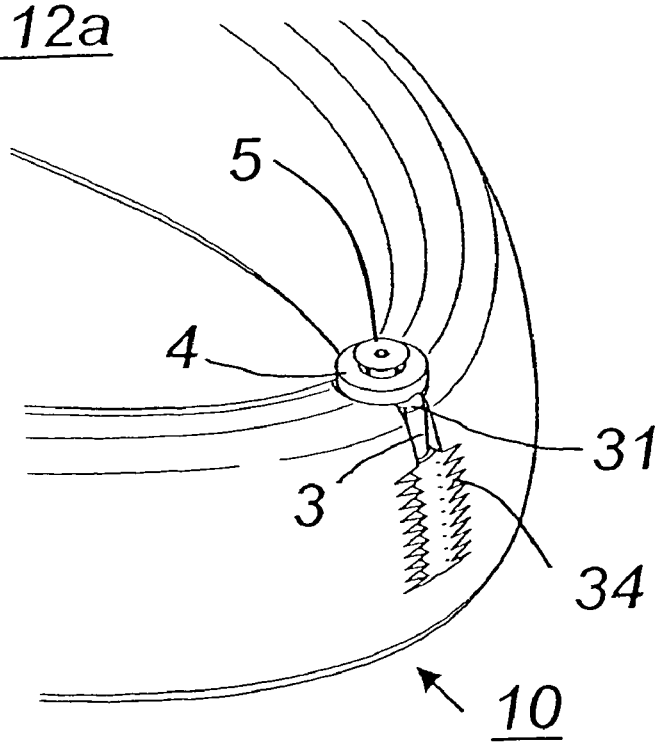

FIG. 11 illustrates the implant site after the removal of the grooving devices 91 and the supporting fixture 90, wherein it will be seen that the jawbone 10 is formed with the conical socket 13 for receiving the conical implant segment 2, with the lateral slot 13a for receiving the lateral implant segment 3, and with the plurality of horizontal grooves 15 for receiving the ribs 34 of the lateral implant segment 3.

After the jawbone has been so prepared, the various elements of the implant shown in FIG. 1 are then applied. Thus, conical implant segment 2 is inserted into socket 13; the spherical end 31 of the lateral implant segment 3 is inserted into the upper end 25a of the lateral slot 25 in the conical implant segment 2; and the lateral implant segment 3 is then rotated downwardly to firmly seat its ribs 34 into the grooves 15 formed in the jawbone. The cover 4 is then applied with its central bore 43 aligned with bore 24 of the conical implant segment 2, and with its semi-spherical recess 44 engaging the spherical element 31 of the lateral implant segment 3. The fixing screw 5 is then threaded through bore 43 in the cover 4 and bore 24 in the conical implant segment 2 to fix the assembly in place.

After the required period of time for osseointegration to take place (approximately three months for the mandible and about six months for the maxilla), the implant is used for mounting the prosthetic device in the following manner:

The screw 5 and cover 4 are removed, and an abutment 98 is applied instead of a cover by the use of an abutment pin 99, as shown in FIG. 13. The abutment 98 is formed with a central bore 98a and with a semi-spherical recess 98b on its inner face to face the semi-spherical element 31 at the end of the lateral implant segment 3. Abutment pin 99 includes an upper section 99a of complementary configuration to the bore 98a in the abutment 98, and a lower threaded section 99b which extends through the inner face of the abutment 98 for threading into the bore 24 of the conical implant segment 2, and with the semi-spherical recess 98b of the implant firmly engaging the semi-circular element 31 at the upper end of the lateral implant segment 3. As shown in FIGS. 13 and 13a, the outer end of the abutment pin 99a is formed with a tabbed bore for receiving a removable screw 99c, which screw may be removed when mounting the prosthetic device in the conventional manner.

FIG. 14 illustrates the implant with the abutment 98 mounted thereto preparatory to receiving the prosthetic device.

While the invention has been described with respect to one preferred embodiment, it will be appreciated that this is set forth merely for purposes of example, and that many other variations and applications of the invention may be made. Thus, the invention could be used in other types of implants in bones, for example in finger bones. Many other variations and applications will be apparent.

What is claimed is:

1. A bone implant, comprising: a main implant segment to be received in a cavity formed in a first face of the bone, and a lateral implant segment having one end to be seated on the main implant segment, and carrying at its opposite end at least one projection to be received in a groove formed in a second face of the bone laterally of said cavity for providing lateral support of said main implant segment when implanted into the bone, wherein said main implant segment is formed with a central bore in one end face for attaching a prosthetic device thereto when the main implant segment is implanted into the bone, and with a lateral slot extending along one side of the main implant segment from said one face to the opposite end face of the main implant segment for receiving said lateral implant segment.

2. The implant according to claim 1, wherein said main implant segment is of conical configuration.

3. The implant according to claim 1, wherein said lateral slot includes a rounded section at said one end face of the main implant segment, and a generally cylindrical section extending from said one end face to said opposite end face; and wherein said lateral implant segment includes a rounded section at said one end for seating on said rounded section of said lateral slot, and a cylindrical section for reception in said cylindrical section of the lateral slot.

4. The implant according to claim 3, wherein said cylindrical section of the lateral slot, and said cylindrical section of the lateral implant segment, are each formed with a pair of opposed flat faces to prevent rotation of the lateral implant segment within said lateral slot.

5. The implant according to claim 1, wherein said implant is a dental implant and is dimensioned to be implanted into the jawbone of a subject, said main implant segment being of a shallow height such as to be contained within the compact bane tissue of the jawbone, and not to penetrate into the medullary or soft spongy tissue of the jawbone.

6. A bone implant, comprising: a main implant segment to be received in a cavity formed in a first face of the bone, and a lateral implant segment having one end to be seated on the main implant segment, and carrying at its opposite end at least one projection to be received in a groove formed in a second face of the bone laterally of said cavity for providing lateral support of said main implant segment when implanted into the bone, wherein said at least one projection in the opposite end of the lateral implant segment includes a plurality of spaced parallel ribs receivable in a plurality of grooves formed in said second face of the bone.

7. The implant according to claim 6, wherein said ribs are of decreasing thickness toward their outer edges.

8. A bone implant, comprising: a main implant segment to be received in a cavity formed in a first face of the bone, and a lateral implant segment having one end to be seated on the main implant segment and carrying at its opposite end at least one projection to be received in a groove formed in a second face of the bone laterally of said cavity for providing lateral support of said main implant segment when implanted into the bone, wherein said lateral implant segment is secured to said main implant segment by a cover overlying said main implant segment and said one end of the lateral implant segment after its projection is received in said groove in the bone.

9. A method of making an implant in a bone of a subject, comprising: drilling a cavity in a first face of the bone;
   forming at least one groove in a second face of the bone laterally of said cavity;
   inserting into said cavity a main implant segment formed with a lateral slot extending through and along one side of the main implant segment from one end face to the opposite end face thereof;
   seating on said one end face of the main implant segment one end of a lateral implant segment with the lateral implant segment extending along said lateral slot past said opposite end face of the main implant segment and formed with at least one projection to be received in said groove formed in the bone; and
   securing said lateral implant segment to said main implant segment for a period of time to permit osseointegration of said segments to the bone.

10. The method according to claim 9, wherein said implant is a dental implant to be applied to the jawbone of the subject, and said cavity is drilled into the jawbone to a relatively shallow depth such as to terminate short of the medullary or soft spongy tissue of the jawbone.

11. The method according to claim 9, wherein said lateral implant segment is secured to said main implant segment by a cover overlying said main implant segment and said one end of the lateral segment after received in said lateral slot.

12. The method according to claim 9, wherein said lateral implant segment is formed with a plurality of projections receivable in correspondingly formed grooves in the jawbone.

13. The method according to claim 9, wherein the cavity drilled in said bone is of conical configuration for receiving a main implant segment of conical configuration.

14. The method according to claim 9, wherein said at least one groove is formed in said bone by the use of an accessory received in said cavity in the bone, and a supporting fixture mounted on said accessory for supporting a grooving device laterally of said cavity.

15. A kit for use in making implants into a bone, comprising:
a main implant segment to be received in a cavity in the bone;
and a lateral implant segment to be seated at one end on the main implant segment, and carrying at least one projection at the opposite end to be received in a groove formed in the bone laterally of said cavity for providing lateral support to said main implant segment when implanted into the bone, wherein said kit further includes a cover to be applied over both segments, and a fixation screw for securing said cover to both said segments.

16. The kit according to claim 15, wherein said kit further includes an accessory to be received in said cavity in the bone and having the same configuration as said main implant segment; and a supporting fixture mountable on said accessory for supporting a grooving device laterally of said cavity to produce at least one groove in said bone for receiving said projection of the lateral implant segment.

17. The kit according to claim 16, wherein said supporting fixture includes a pair of plates supported in parallel spaced relation to each other and formed with aligned slots for receiving said grooving device.

* * * * *